United States Patent [19]
Brown, Jr.

[11] Patent Number: 5,566,435
[45] Date of Patent: Oct. 22, 1996

[54] METHOD OF ATTACHING A TAMPON WITHDRAWAL CORD WITH AN OVERHAND HITCH KNOT

[75] Inventor: Robert W. Brown, Jr., Hampden, Mass.

[73] Assignee: Tambrands Inc., White Plains, N.Y.

[21] Appl. No.: 535,620

[22] Filed: Sep. 28, 1995

Related U.S. Application Data

[62] Division of Ser. No. 225,669, Apr. 1, 1994.

[51] Int. Cl.$^6$ ..................................... A61F 13/34
[52] U.S. Cl. ................. 28/120; 289/1.5; 100/2; 604/385.1; 604/904
[58] Field of Search ............... 28/118, 120, 119; 289/1.5, 2, 5, 12, 15; 604/384, 385.1, 904; 53/585, 138.6, 138.7, 138.8; 100/2, 33 R, 1, 7

[56] References Cited

U.S. PATENT DOCUMENTS

| | | | |
|---|---|---|---|
| 2,286,817 | 6/1942 | Knight | 128/285 |
| 2,455,925 | 12/1948 | Ganz | 18/55 |
| 2,458,685 | 1/1949 | Crockford | 18/55 |
| 2,584,913 | 2/1952 | Parish | 28/21 |
| 2,763,899 | 9/1956 | Niepmann et al. | 19/144.5 |
| 2,913,270 | 11/1959 | Sachsenroder, Sr. et al. | 289/2 |
| 2,938,519 | 5/1960 | Marco | 128/285 |
| 3,212,800 | 10/1965 | Freudling | 289/1.5 |
| 3,320,956 | 5/1967 | Steiger | 128/263 |
| 3,431,919 | 3/1969 | Krusko | 128/285 |
| 3,814,469 | 6/1974 | Simon | 289/1.5 |
| 4,108,299 | 8/1978 | Mast, Jr. | 28/119 |
| 4,222,381 | 9/1980 | Widlund et al. | 128/270 |
| 4,836,587 | 6/1989 | Hinzmann | 289/2 |
| 5,084,038 | 1/1992 | Sheldon et al. | 28/120 |
| 5,149,332 | 9/1992 | Walton et al. | 604/358 |
| 5,364,383 | 11/1994 | Hayes et al. | 604/384 |

FOREIGN PATENT DOCUMENTS

| | | |
|---|---|---|
| 1163752 | 3/1984 | Canada . |
| 2612488 | 9/1977 | Germany . |
| 2926130 | 1/1981 | Germany . |
| 460257 | 9/1989 | Sweden . |
| 324888 | 11/1957 | Switzerland . |

OTHER PUBLICATIONS

Fry, Knots and Ropework, 1977.

Primary Examiner—C. D. Crowder
Assistant Examiner—Larry D. Worrell, Jr.
Attorney, Agent, or Firm—Fish & Richardson P.C.

[57] ABSTRACT

An improved knot for attachment of withdrawal cords to tampons is provided. The knot comprises at least two closed loops around a portion of a length of absorbent material. The standing parts of the cord cross at least twice, to form a crossed portion at the base of the loops; a loop portion overlies the crossed portion when the knot is in place around the absorbent material, applying pressure to the crossed portion when the knot is tightened. The invention also features a process for forming the knot.

9 Claims, 7 Drawing Sheets

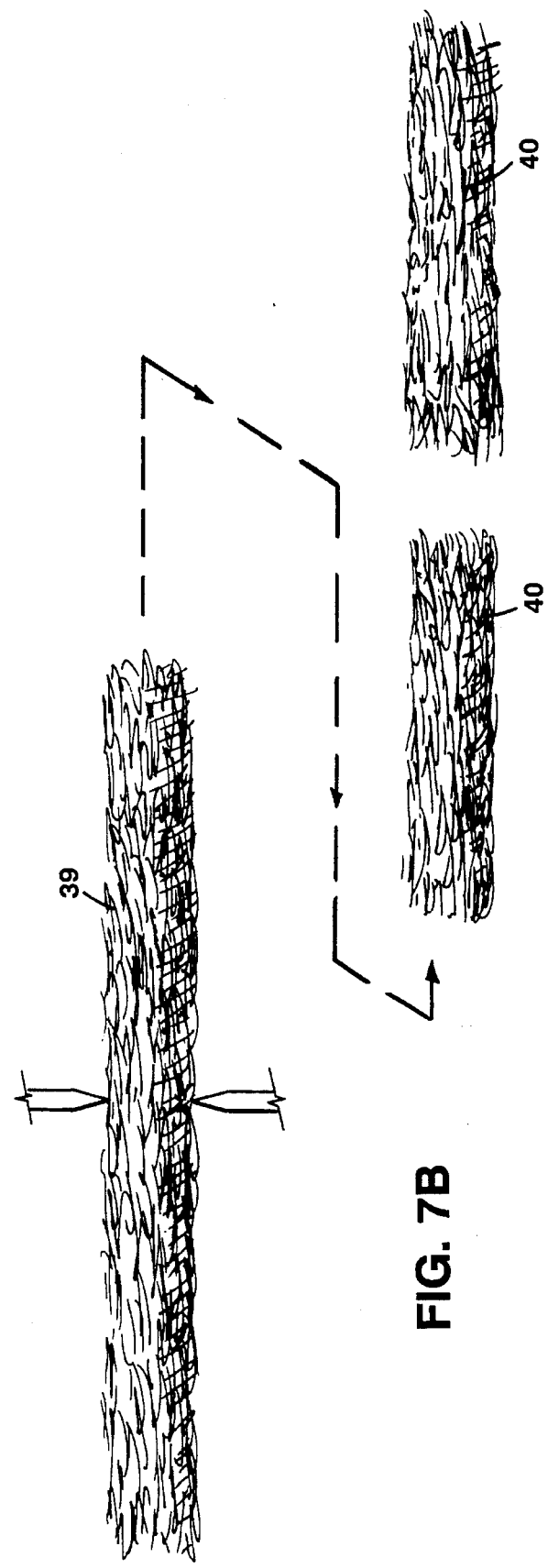
FIG. 7A
FIG. 7B

METHOD OF ATTACHING A TAMPON WITHDRAWAL CORD WITH AN OVERHAND HITCH KNOT

This is a divisional of application Ser. No. 08/225,669, filed Apr. 11, 1994.

BACKGROUND OF THE INVENTION

The invention relates to methods and knots for attaching a withdrawal cord to a tampon, e.g., a catamenial tampon.

Tampons are typically manufactured by cutting an absorbent material into a desired length, attaching a withdrawal cord to the length of material, forming the length of material into a pledget, and compressing the pledget. The absorbent material may comprise short fibers provided in the form of a nonwoven web, or a bundle of continuous long filaments, i.e., a "filament tow". Filament tow tampons are described in, e.g., U.S. Pat. Nos. 3,177,872, 3,320,956, and 2,934,068. The withdrawal cord has been attached in a number of different ways, e.g., by a row of stitching or by looping the cord over the material and folding or rolling the material around the loop.

One step in the manufacture of filament tow tampons is the knotting of a withdrawal cord at the approximate midpoint of the length of absorbent material. Typically, a length of cord is doubled to form a loop, the doubled cord is passed around the material, and the ends of the cord are drawn through the loop, forming a ring or girth hitch, as shown in FIG. 1.

Canadian Patent 1,163,752 proposes the use of other types of knots, e.g., clove and prussic hitches, to prevent telescoping in spirally wound tampons.

All of these conventional knots are difficult to form in a continuous process, i.e., it is difficult or impossible to form a plurality of knots in a continuous length of cord without cutting or breaking the cord. Accordingly, application of the withdrawal cord tends to be the limiting factor in high speed tampon manufacturing processes.

SUMMARY OF THE INVENTION

The invention features an improved knot for attachment of withdrawal cords to tampons. The knot can be tied in a continuous cord, without needing to thread a free end, and a plurality of knots can be formed at once without severing or breaking the cord. Thus, preferred knot forming processes of the invention can run at very high speeds. Moreover, preferred knots will slip out of the cord if no absorbent material is present for the knot to tighten around, providing another advantage in high speed continuous processing.

Advantageously, the knot cinches tight around the absorbent material and remains tight during storage and use. It has been found that the provision of a tight knot around a portion of the absorbent material (preferably at the base of the tampon) unexpectedly improves the tampon's absorbency and resistance to premature leakage.

The knot of the invention is referred to herein as an "overhand hitch". The overhand hitch comprises at least two closed loops around a portion of a length of absorbent material. The standing parts of the cord (i.e., the portions of the cord which extend away from the looped portion in each direction) cross at least twice, defining a crossed portion at the base of the loops, and extend in opposite directions from said crossed portions; a loop portion overlies the crossed portion when the knot is in place around the absorbent material, applying pressure to the crossed portion when the knot is tightened. Preferably, the standing parts cross twice, so that the crossed portion resembles an overhand knot.

The invention also features a process for forming the knot. The process includes forming an S-shaped curve in a cord, crossing the standing parts of the cord over the curve to form a crossed portion interposed between two opposed loops, folding the loops together around the crossed portion, inserting a length of absorbent material through the two loops, and tightening the loops around the material.

In preferred embodiments, the knot is formed in a continuous length of cord. Preferably, the S-shaped curve is formed by placing a pair of spaced members on either side of the cord and rotating the members in a predetermined direction through an arc of approximately 180 degrees; the two closed loops and crossed portion are formed by rotating the members in the same direction, through a further arc of approximately 180 degrees, while lifting the standing parts relative to a horizontal plane defined by the S-shaped curve; and the loops are folded together by tilting the two members from a substantially vertical position to a substantially horizontal position. In a preferred embodiment, the members are hollow cylinders, so that the members, when tilted to their horizontal position, define a bore for receiving the absorbent material. The members can then be separated and removed from the absorbent material, allowing the hitch to be tightened around the material.

The invention further features an improved tampon including the knot of the invention. The tampon includes a compressed pledget of absorbent material, shaped for insertion into a body cavity, and a withdrawal cord attached to the tampon by an overhand hitch. In a preferred embodiment, the pledget, prior to compression, includes an absorbent material derived from a filament tow of substantially hydrophilic filaments. Preferably, the filaments have a substantially permanently crimped configuration, and are disposed in a randomly out-of-phase orientation with respect to each other so as to increase the average pore volume ratio, i.e., the fraction of volume occupied by interfilament spaces or interstices between filaments, of the pledget. Preferably the average pore volume ratio of the compressed tampon is in the range of 60 to 95%, more preferably 70 to 90%, and most preferably 80 to 85%.

Other features of the invention will be apparent from the following description of preferred embodiments, and from the claims.

BRIEF DESCRIPTION OF THE DRAWINGS

FIG. 7a–7e diagrammatically illustrate a process for manufacturing a tampon according to one embodiment of the invention.

DESCRIPTION OF THE PREFERRED EMBODIMENTS

Figure 1:
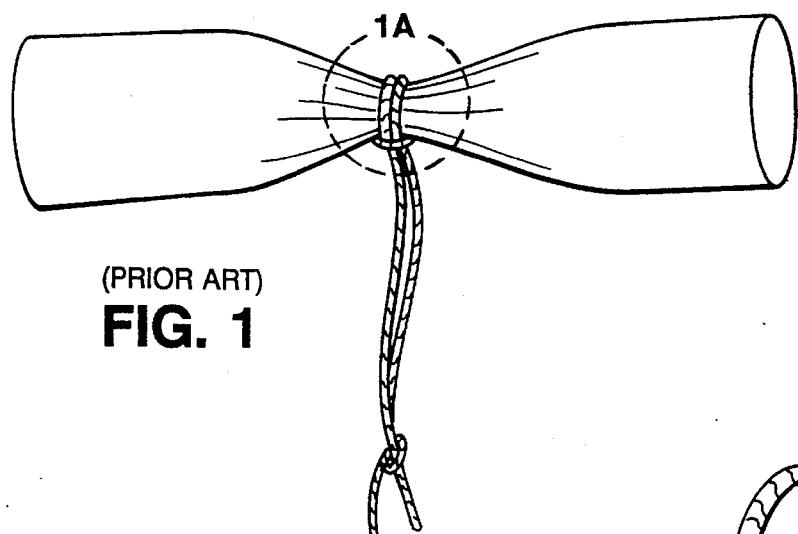
FIG. 1 is a perspective view of a girth hitch according to the prior art.
Figure 1A:
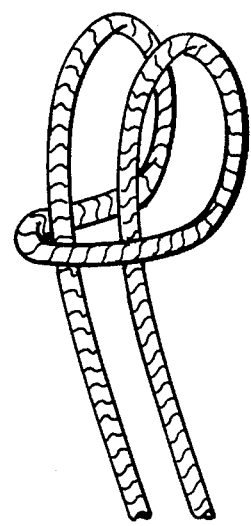
Figure 2:
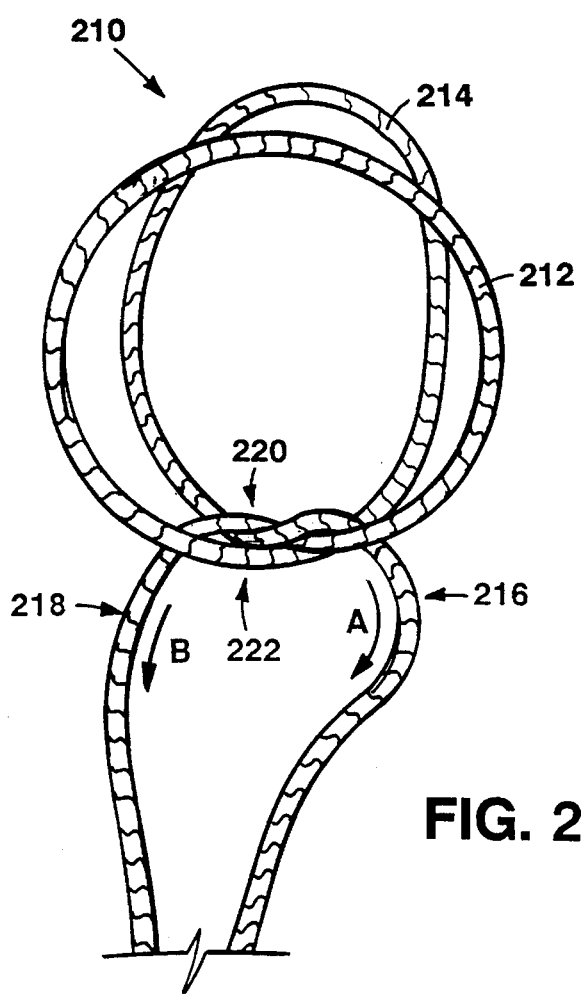
FIG. 2 is a perspective view of a knot according to one embodiment of the invention, shown without absorbent material, for clarity.

Referring to FIG. 2, a preferred knot 210 comprises two closed loops 212, 214. The standing parts 216, 218 of the cord cross at least twice and extend in opposite directions (arrows A, B), to form a crossed portion 220, resembling an overhand knot, at the base of the two loops. A loop portion 222 overlies the crossed portion 220 when the knot is in place around the absorbent material, applying pressure to the crossed portion when the knot is tightened.

Figure 3:
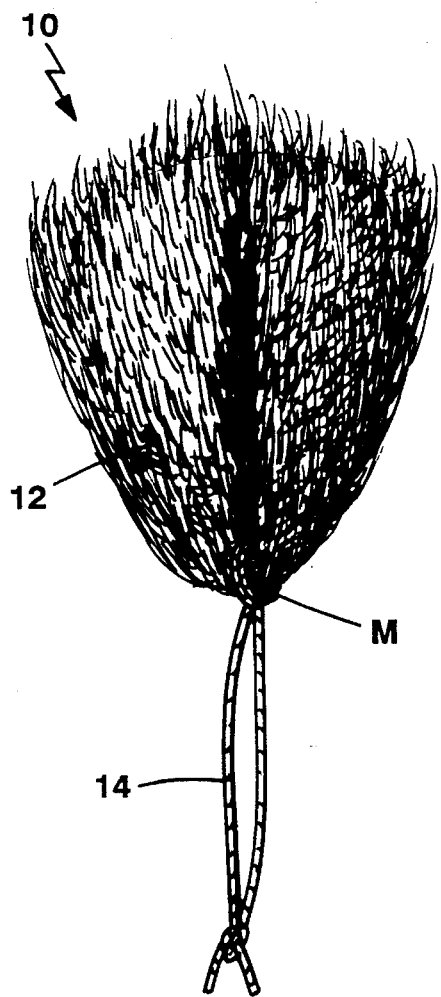
FIG. 3 is a side view of an uncompressed pledget according to one embodiment of the invention.
Figure 4:
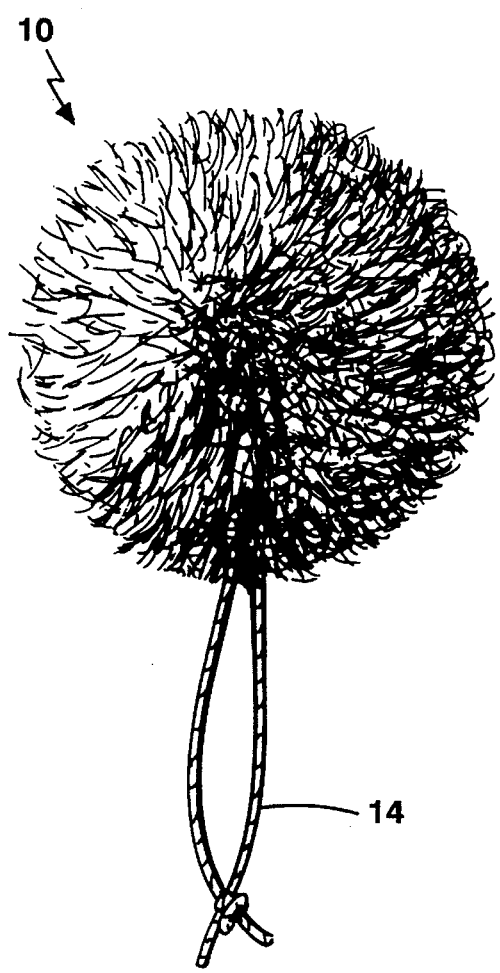
FIG. 4 is a side view of an uncompressed pledget according to another embodiment of the invention.
Figure 7C:
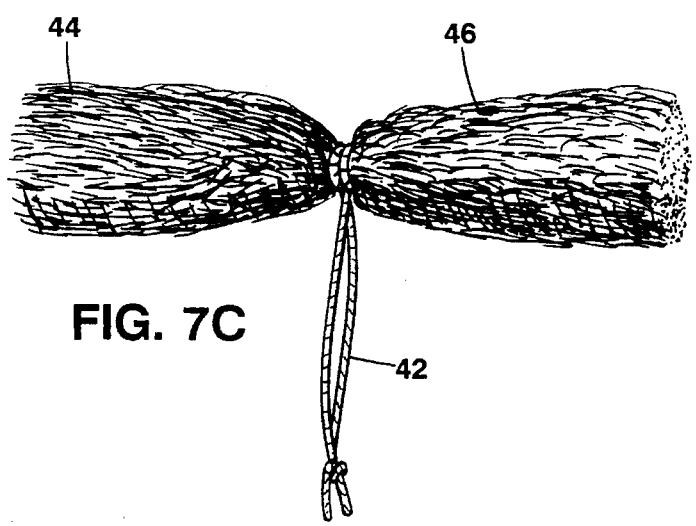

Two preferred pledget configurations are shown in FIGS. 3 and 4 (other configurations are possible). Pledget 10 of FIG. 3, which is most preferred, comprises a length of absorbent material 12, folded in half about a withdrawal cord 14 attached at its approximate midpoint M using the knot shown in FIG. 2. In the alternate embodiment shown in FIG. 4, the filament tow is fluffed around the withdrawal cord, forming a "pom-pom". To form the finished tampon, shown in FIG. 7g, the pledget is compressed substantially radially.

Figure 5:
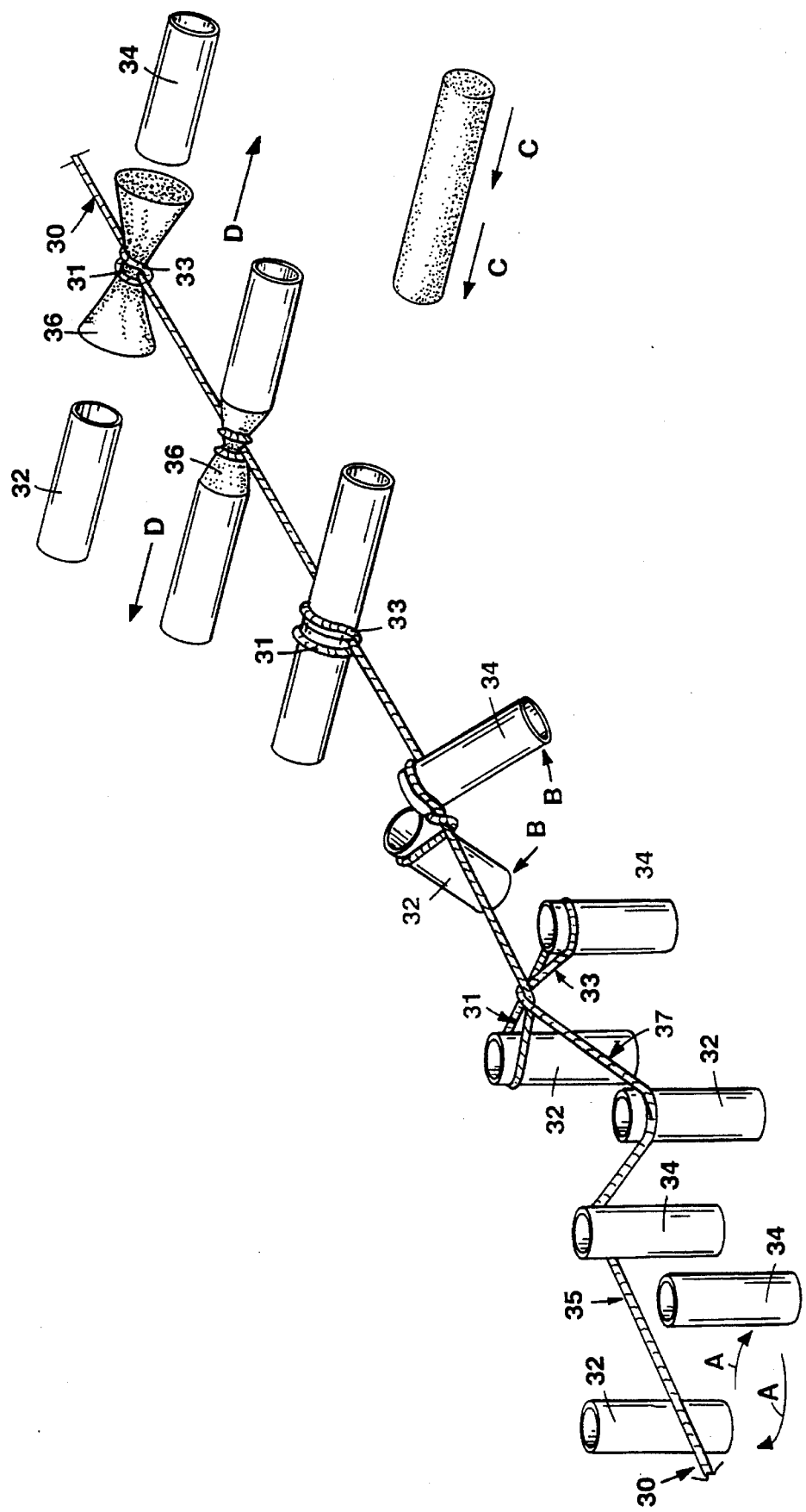
FIG. 5 diagrammatically illustrates a process for attaching a withdrawal cord to a pledget according to one embodiment of the invention.
Figure 5A:
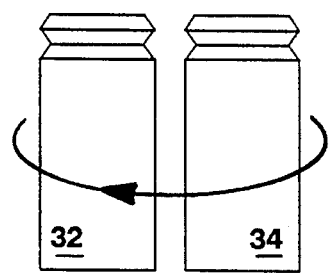
FIGS. 5a–5e diagrammatically illustrate in greater detail a preferred step in the process of FIG. 5.
Figure 5B:
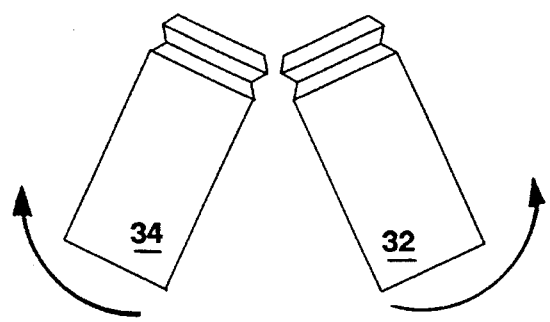
Figure 5C:
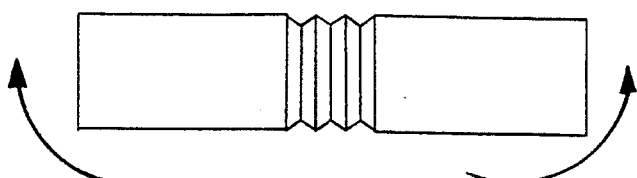
Figure 5D:
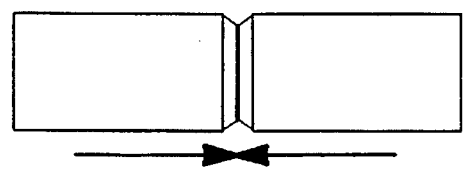
Figure 5E:
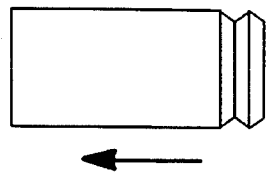
Figure 5E:
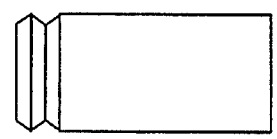

Referring to FIG. 5, a preferred process is shown for applying the withdrawal cord to form the knot shown in FIG. 2. A cord 30 is provided (drawn from a skein or bobbin, not shown), which is continuous, i.e., the cord is not cut into individual lengths prior to formation of the knot around the absorbent material. Hollow cylindrical members 32, 34 are positioned on opposite sides of the cord, with their longitudinal axes substantially vertically oriented. The cylindrical members are then rotated through an arc of about 180 degrees (arrows A), so that their positions are reversed, forming an S-shaped curve in cord 30. Next, the standing parts 35, 37 of the cord (i.e., the portions of the cord extending away from the curve in either direction) are crossed over the curve to form two closed loops 31, 33. This is accomplished by slightly raising the standing parts 35, 37 above the horizontal plane defined by the S-shaped curve, while simultaneously rotating cylindrical members 32, 34 through an additional 180 degree arc in the same direction as the previous rotation, returning them to their initial positions. Then, the loops thus formed are folded together around the crossed standing parts by tilting the cylindrical members so that their longitudinal axes are substantially horizontally oriented (arrows B). The cylindrical members are aligned, in this step, so that their hollow interiors form a cylindrical bore. A length of absorbent material 36 is then inserted through this bore, and thus through the two loops (arrow C). Finally, the cylindrical members are separated and removed (arrows D), and the loops of the cord are tightened around the material.

Figure 5F:
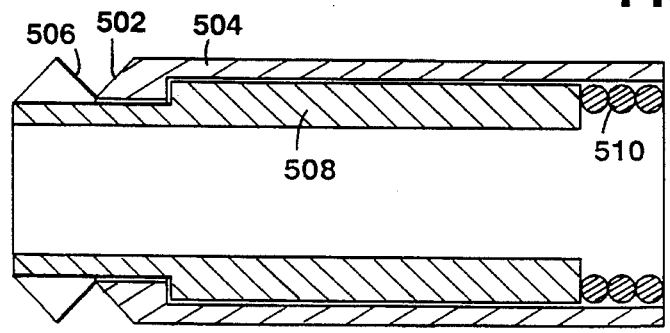
FIG. 5f is a cross-sectional view of one of the cylindrical members used in the step shown in FIGS. 5a–5e.

As shown in FIGS. 5a–5e, the cylindrical members preferably have telescoping portions at their upper ends, to facilitate transfer of the loops of the cord from the cylindrical members to the absorbent material (arrows D in FIG. 5). The inner structure of the cylindrical members is shown in detail in FIG. 5f, which shows a cross-sectional view of one of the members. Each loop of cord passes around the corresponding cylindrical member and is retained in a notch 500 formed by the end surface 502 of an outer tube 504 and an array of angled splines 506 on the outer surface of an inner tube 508. The inner and outer tubes are arranged in a telescoping manner, with the inner tube adapted to be compressed into the outer tube, e.g., by compressing spring 510 (see FIG. 5f). The outer tube is keyed to receive the angled splines on the inner tube, so that, upon compressing the inner tube into the outer tube, the outer tube strips the loop from the inner cylinder by forcing the loop over the angled splines.

Figure 6:
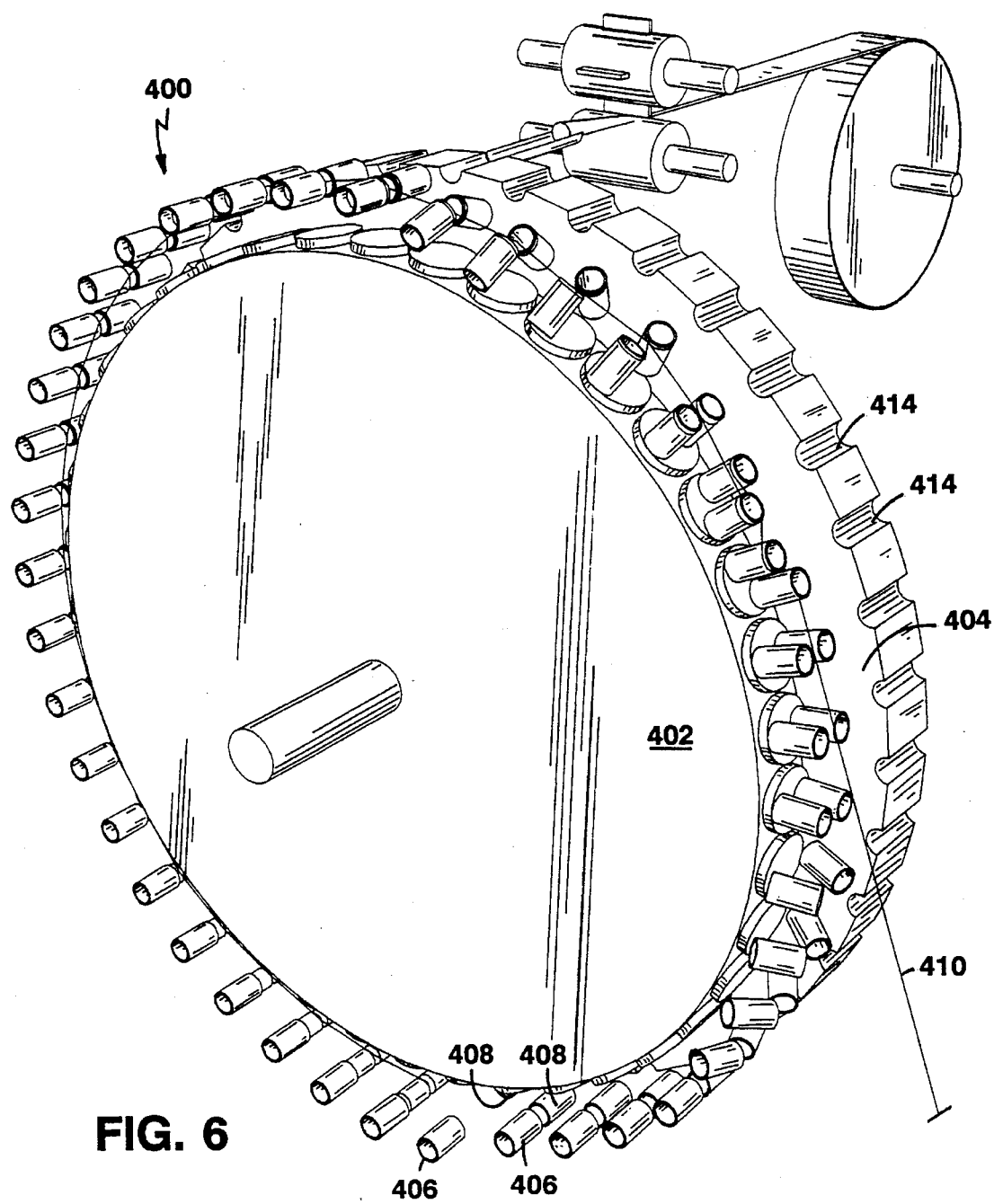
FIG. 6 diagrammatically illustrates the process of FIG. 5 implemented using an apparatus according to one embodiment of the invention.

A preferred apparatus for performing the above-described process is shown in FIG. 6. The apparatus 400 includes a pair of spaced wheels 402, 404. A plurality of pairs of hollow cylindrical members 406, 408 are rotatably mounted at regular intervals about the periphery of the wheel. The cylindrical members are also adapted to pivot from a position in which their longitudinal axes are substantially vertical and parallel, to a position in which their longitudinal axes are substantially horizontal and coincident. As shown, these hollow cylindrical members operate in the manner illustrated diagrammatically in FIG. 9. Wheel 404 includes a plurality of channels 414 spaced to align with the pairs of cylindrical members and shaped to receive a length of absorbent material. Apparatus 400 also includes means (not shown) for transferring a length of absorbent material from a channel 414 to the interior bore formed when the cylindrical members are moved to their substantially horizontal positions, e.g., by pneumatic pressure. The spaced wheels are preferably rotated at substantially the same angular velocity, so that a length of absorbent material can be first delivered to one of the channels 414, then transferred at zero relative velocity to the interior bore defined by the cylindrical members when the channel and bore are aligned. A continuous cord 410 is unwound, e.g., from a bobbin (not shown), to allow a succession of knots to be formed continuously in the manner shown in FIG. 5.

The absorbent material used to form the pledget may be any material which is sufficiently hydrophilic in surface character and absorbent to provide adequate absorption of menstrual fluids when used in a tampon constructed according to the invention. The hydrophilicity of the filaments is determined by the number of available hydroxyl groups present on the surface of the material. It is preferred that the filaments contain at least two available hydroxyl groups per monomer, more preferably at least three. Cellulosic materials have either one (cellulose diacetate), two (cellulose acetate), or three (viscose) hydroxyl groups, and thus viscose is preferred. Preferably, the material has a water imbibition value of at least 40%, more preferably at least 90%. Absorption tends to be more dependent on hydrophilicity (which affects water storage between filaments) than on absorptivity (which affects water storage within filaments), and thus non-absorptive filaments can be used as long as they are sufficiently hydrophilic.

It is also preferred that the filaments be formed of a material in which a substantially permanent crimp can be set. By "substantially permanent crimp", it is meant that the individual filaments have a random sinuous configuration. The filaments are given this sinuous configuration in a manner which imparts a rigidity to the crimp, i.e., prevents the crimp from being readily removed by pulling or wetting of the filament or filament tow. The permanence of the crimp is defined by its substantial recovery after extension to but not beyond the elastic limit of the crimp of the individual filaments. The crimp can be achieved in several ways, e.g., by overfeeding into a spreader box (or stuffer box) during cellulose regeneration, by heat setting, by chemical means, or by mechanical means (e.g., by using known compressive crimping processes such as SANFORISING, MICREX, or CLUPAK crimping processes, in which a tow is overfed into a space formed between two rollers and a feed shoe, causing the tow to buckle, or by processing the filaments through gear elements). What is important is that the crimp be substantially permanent so that it is difficult to remove from the filaments during processing.

A particularly preferred filament material is viscose. Viscose has three available hydroxyl groups per monomer, and has a water imbibition value of about 95 to 280%. Viscose can be permanently crimped during regeneration.

Other materials, e.g., synthetic, thermoplastic filaments and other cellulosic filaments (e.g., cellulose acetate), could be used if they are processed (e.g., by being given a surface treatment) so as to be substantially hydrophilic. Thermoplastic synthetic filaments and cellulosic filaments such as cellulose acetate can successfully be crimped by heat set and mechanical techniques. Super-inflated filaments can be used, i.e., hollow filaments spun to include a lumen, as described in British Patent Application No. 2,022,505.

In some preferred embodiments, the degree of the out of phase relationship between filaments is increased prior to incorporation of the absorbent material into the pledget by blooming the filament tow, preferably by pulling it along its longitudinal dimension and then allowing it to relax. The pulling is enough to separate the individual crimped filaments into a more out of phase relationship, but not so much as to exceed the elastic limit of the crimp (and thereby remove the crimp).

As shown in FIG. 7a, the filament tow is bloomed by pulling it longitudinally, and then allowing it to relax. Preferably, the blooming is done using a known blooming process in which the filament tow is passed through a tube through which an air stream flows. The resistance of the tow to the flowing air provides a controlled lengthwise pulling action, followed by relaxation as the bloomed web emerges at the downstream end of the tube. Alternatively, the tow web can be bloomed by any other method which produces a filament tow with the desired randomly out-of-phase relationship between filaments, e.g., by stretching an overfed web in other directions than longitudinally, or by using fluid-jet entangling or air entangling to produce the filament tow. The longitudinal stretching force used to bloom the web is high enough to break apart the filament relationships in the overfed web, but not so high as to exceed the elastic limit of the crimp (and thus lose the crimp set in the filaments).

The resulting bloomed filament tow has greatly increased average pore volume. The blooming produces a randomly out-of-phase relationship between the sinuous, crimped filaments, so that peaks and valleys of adjacent filaments are not as aligned as they were in the overfed web. By "randomly out-of-phase", it is meant that the sinuous configuration of individual crimped filaments is randomly out of phase with respect to that of neighboring filaments, i.e., that the peaks and valleys of the filaments are randomly misaligned, with resulting increase in the volume of interfilament spaces (i.e., the average pore volume). Precise mathematical randomness is not required, only substantial variability in the alignment of peaks and valleys. Preferably, the bloomed filament tow has a average pore volume ratio of at least 95%. The term "average pore volume ratio" as used herein refers to the fraction of space within a structure (e.g., the uncompressed pledget or the compressed tampon) that comprises the interfilament spaces or interstices. The ratio is calculated as a percentage by the following formula:

$$\frac{\text{total volume} - \text{volume of filaments}}{\text{total volume}} \times 100$$

Preferably, the average pore volume ratio of the uncompressed pledget is greater than 95%, more preferably greater than 96%. The average pore volume ratio of the compressed tampon is lower, most preferably in the range of 80 to 85%.

After stretching, the filament tow is cut into lengths 40 (FIG. 7b), each preferably about 90 to 120 mm, more preferably about 100 to 110 mm long. Cutting can be accomplished using standard equipment, such as that used to cut absorbent materials in conventional tampon manufacture.

Alternatively, instead of stretching/relaxing the entire tow prior to cutting, the lengths of absorbent material can be stretched/relaxed individually after cutting (i.e., steps FIG. 7a and 7b can be reversed). However, this is likely to result in a less consistent final product, and cutting the unstretched tow may result in cutting individual filaments in more than one place, causing parts of these filaments to fall off. Also, the material may be cut while it is maintained under tension, and then the individual lengths allowed to relax before further processing.

After the tow has been stretched and cut to length, a withdrawal cord 42 is attached to each length using an overhand hitch. Preferably, the cord 42 is attached at approximately the midpoint M of the length (FIG. 7c), and is tied relatively tightly around the absorbent material, causing the tied area to be densified in the finished tampon. The overhand hitch may be formed by the preferred method or in any other suitable manner. Optionally, prior to attachment of the withdrawal cord the length of material can be rolled or folded longitudinally (not shown).

Figure 7D:
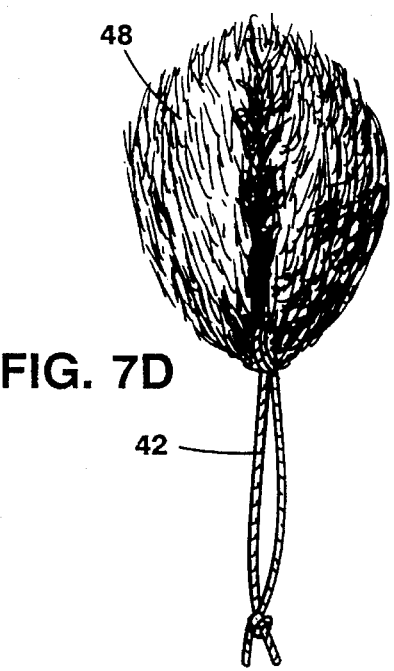

The two ends 44, 46 of the length are then folded together (FIG. 7d) to form the pledget 48.

Figure 7E:
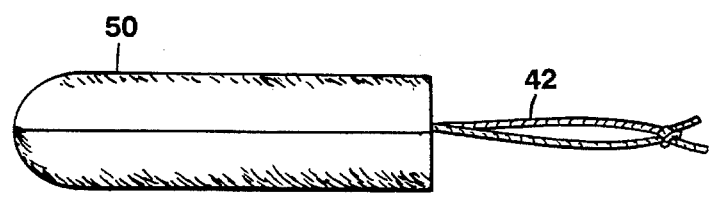

Finally, pledget 48 is radially compressed, to form tampon 50 (FIG. 7e). By "compressed", it is meant that the pledget is compressed to an extent such that it does not exhibit a significant amount of expansion during storage at ambient conditions, i.e., room temperature, atmospheric pressure and 50% relative humidity. Preferably, the pledget is compressed sufficiently to prevent it from expanding more than 65% of its initial compressed volume over 48 hours under ambient conditions. This degree of compression is typically achieved by compressing the pledget to a bulk density of at least 0.05 g/cc, more preferably from about 0.1 to 0.6 g/cc, most preferably 0.2 to 0.4 g/cc. It is preferred that the compressed pledget have a bulk density of at least 0.05 g/cc, more preferably 0.1 to 0.6 g/cc, and most preferably 0.2 to 0.4 g/cc.

Other embodiments are within the claims. For example, while the processes illustrated in FIGS. 5 and 6 are preferred, other processes may be used to form the overhand hitch. The hitch may be used in tampon configurations other than those shown, e.g., in spirally wound tampons, and may be used with other types of absorbent materials, e.g., chopped fiber webs. The knot may have a more complex structure, provided it has at least two loops and the standing ends are crossed at least twice. For example, the knot may have more than two loops, and in the crossed portion the standing parts may cross each other more than twice. The knot may be applied to other products, in addition to tampons.

I claim:

1. A method for forming a tampon, shaped for insertion into a body cavity, comprising the steps of:

providing a cord;

forming an S-shaped curve in said cord a portion of said cord extending from each side of the S-shaped curve to define a pair of standing parts;

crossing the standing parts of the cord over the curve to form two opposed loops;

folding the loops together around the crossed standing parts;

inserting a length of absorbent material through the two loops; and tightening the loops around the material to form an overhand hitch.

2. The method of claim 1 wherein the S-shaped curve is formed by placing a pair of spaced members on either side of said cord and rotating said members in a predetermined direction through an arc of approximately 180 degrees.

3. The method of claim 2 wherein said two loops and said crossed standing parts are formed by rotating the members, in the same direction, through a further arc of approximately 180 degrees, while lifting the standing parts relative to a horizontal plane defined by the S-shaped curve.

4. The method of claim 2 or 3 wherein said loops are folded together by tilting said two members from a substantially vertical position to a substantially horizontal position.

5. The method of claim 4 wherein said members are hollow cylinders, so that the members, when tilted to their horizontal position, define a bore for receiving the absorbent material.

6. The method of claim 5 further comprising the step of separating and removing the members from the absorbent material, allowing the hitch to be tightened around the material.

7. The method of claim 1 wherein a plurality of overhand hitches are formed from an unsevered cord around a plurality of tampons.

8. The method of claim 1 wherein said forming, crossing, and folding steps are performed at a plurality of stations along an unsevered length of said cord so as to form a plurality of overhand hitches that may be formed around lengths of absorbent material.

9. The method of claim 7 or 8 wherein the plurality of overhand hitches are equally spaced along the unsevered cord.

* * * * *

UNITED STATES PATENT AND TRADEMARK OFFICE
CERTIFICATE OF CORRECTION

PATENT NO.   : 5,566,435

DATED        : October 22, 1996

INVENTOR(S)  : Robert W. Brown, Jr.

It is certified that error appears in the above-identified patent and that said Letters Patent is hereby corrected as shown below:

Cover page, [62] Related U.S. Application Data, "Apr. 1, 1994" should be --Apr. 11, 1994--.

Signed and Sealed this

Twenty-fifth Day of February, 1997

Attest:

BRUCE LEHMAN

*Attesting Officer*  *Commissioner of Patents and Trademarks*